US012778871B2

(12) United States Patent
Nicou et al.

(10) Patent No.: US 12,778,871 B2
(45) **Date of Patent: *Nov. 3, 2026**

(54) COSMETIC COMPOSITION COMPRISING A COMBINATION OF TWO PARTICULAR COUPLERS AND N,N-DICARBOXYMETHYLGLUTAMIC ACID AND/OR ITS SALTS

(71) Applicant: L'Oreal, Paris (FR)

(72) Inventors: Valerie Nicou, Saint Ouen (FR); Robin Protat, Saint Ouen (FR)

(73) Assignee: L'Oreal, Paris (FR)

( * ) Notice: Subject to any disclaimer, the term of this patent is extended or adjusted under 35 U.S.C. 154(b) by 326 days.

This patent is subject to a terminal disclaimer.

(21) Appl. No.: 18/257,841

(22) PCT Filed: Dec. 16, 2021

(86) PCT No.: PCT/EP2021/086233

§ 371 (c)(1),
(2) Date: Jun. 15, 2023

(87) PCT Pub. No.: WO2022/129352

PCT Pub. Date: Jun. 23, 2022

(65) Prior Publication Data

US 2024/0074960 A1 Mar. 7, 2024

(30) Foreign Application Priority Data

Dec. 17, 2020 (FR) .................................... 2013533

(51) Int. Cl.

| | |
|---|---|
| ***A61Q 5/10*** | (2006.01) |
| ***A61K 8/22*** | (2006.01) |
| ***A61K 8/41*** | (2006.01) |
| ***A61K 8/44*** | (2006.01) |
| ***A61K 8/49*** | (2006.01) |
| ***A61Q 5/08*** | (2006.01) |

(52) U.S. Cl.

CPC .............. *A61K 8/4973* (2013.01); *A61K 8/44* (2013.01); *A61Q 5/10* (2013.01); *A61K 2800/30* (2013.01); *A61K 2800/4324* (2013.01); *A61K 2800/882* (2013.01)

(58) Field of Classification Search

CPC ............ A61Q 5/10; A61Q 5/08; A61Q 5/065; A61K 2800/882; A61K 8/22; A61K 2800/88; A61K 2800/43; A61K 2800/4324; A61K 2800/4322

See application file for complete search history.

(56) References Cited

U.S. PATENT DOCUMENTS

| | | | | |
|---|---|---|---|---|
| 5,344,463 | A * | 9/1994 | Chan ...................... | A61K 8/347 8/408 |
| 8,523,956 | B2 | 9/2013 | Wood et al. | |
| 2013/0220358 | A1 * | 8/2013 | Agostino ................. | A61Q 5/10 8/408 |
| 2018/0153780 | A1 | 6/2018 | Azizova et al. | |
| 2020/0163851 | A1 | 5/2020 | Nicou et al. | |

FOREIGN PATENT DOCUMENTS

| | | |
|---|---|---|
| CN | 105596228 | 5/2016 |

OTHER PUBLICATIONS

PubChem, 6-hydroxybenzomorpholine, accessed Jul. 7, 2025 (Year: 2025).*

PubChem,hydroxyethyl-3,4-methylenedioxyaniline, accessed Jul. 7, 2025 (Year: 2025).*

Katiuscia Grevalcuore et al., "Hair Care Composition," Research Disclosure, Kenneth Mason Publications, vol. 672, No. 75, (Apr. 1, 2020), XP007148274, (4 pages).

International Search Report for PCT/EP2021/086233 (International Filing Date: Dec. 16, 2021), mailed Mar. 31, 2022 (3 pages).

* cited by examiner

*Primary Examiner* — Tracy Liu

(74) *Attorney, Agent, or Firm* — CHRISTENSEN O'CONNOR JOHNSON KINDNESS PLLC

(57) ABSTRACT

A subject of the present invention is a cosmetic composition comprising 6-hydroxybenzornorpholine of formula (II), hydroxyethyl-3,4-methylenedioxyaniline of formula (III), at least one compound chosen from N,N-dicarboxymethylglutamic acid, its salts and mixtures thereof.

The present invention also relates to a process for dyeing keratin fibres, such as the hair, wherein the composition as described previously is applied to said fibres.

Another subject of the present invention is the use of the composition according to the invention for the cosmetic treatment of keratin fibres such as the hair.

18 Claims, No Drawings

COSMETIC COMPOSITION COMPRISING A COMBINATION OF TWO PARTICULAR COUPLERS AND N,N-DICARBOXYMETHYLGLUTAMIC ACID AND/OR ITS SALTS

CROSS-REFERENCES TO RELATED APPLICATIONS

This application is a National Stage of International Application No. PCT/EP2021/086233, filed Dec. 16, 2021, which claims priority to FR 2013533, filed Dec. 17, 2020, the entire contents of which are incorporated by reference herein in their entirety.

A subject of the present invention is a cosmetic composition comprising 6-hydroxybenzomorpholine of formula (II), hydroxyethyl-3,4-methylenedioxyaniline of formula (III), and N,N-dicarboxymethylglutamic acid, and/or its salts.

The present invention also relates to a process for dyeing keratin fibres, such as the hair, wherein the composition as described previously is applied to said fibres.

Another subject of the present invention is the use of the composition according to the invention for the dyeing of keratin fibres such as the hair.

It is known practice to dye keratin fibres and in particular human hair with dye compositions containing oxidation dye precursors, such as oxidation bases, notably ortho- or para-phenylenediamines, ortho- or para-aminophenols and heterocyclic compounds. These oxidation bases are colourless or weakly coloured compounds, which, when combined with oxidizing products, are able to produce coloured compounds by a process of oxidative condensation.

It is also known that the shades obtained with these oxidation bases may be varied by combining them with couplers or colour modifiers, the latter being notably chosen from aromatic meta-diaminobenzenes, meta-aminophenols, meta-diphenols and certain heterocyclic compounds such as indole compounds.

The variety of molecules used as oxidation bases and couplers allows a wide range of colours to be obtained.

"Permanent" dyeing is characterized by the use of oxidation dye precursor(s) (bases and/or couplers) in the presence of oxidizing compound(s). In order to be considered as efficient dyeing, the latter needs to satisfy certain criteria. It must make it possible to obtain shades in the desired intensity with colour differences, between the end and the root of the same lock (also known as the selectivity), which are as small as possible.

The colouring must also be resistant over time and must not become degraded in the presence of external agents such as washing, light, bad weather, rubbing and perspiration.

However, the dyeing results obtained are not always very satisfactory, especially in terms of selectivity, of colour build-up, in particular for ensuring good coverage of the hair, more particularly of white hair, of chromaticity, of intensity and/or of persistence, in particular with respect to successive shampooing operations, or of resistance to light or to perspiration.

There is thus a real need to develop compositions that can dye keratin fibres in an intense, persistent, sparingly selective and chromatic manner, with good build-up of the colour, and which are capable of giving colourings that are resistant to the various attacking factors to which the fibres may be subjected, such as bad weather, washing and perspiration, and are also capable of resulting in good dyeing performance even after a period of storage.

A subject of the present invention is thus a cosmetic composition comprising:

at least one oxidation coupler chosen from 6-hydroxybenzomorpholine of formula (II) below, one of its addition salts, its solvates and/or solvates of its salts:

(II)

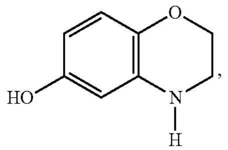

at least one oxidation coupler chosen from hydroxyethyl-3,4-methylenedioxyaniline of formula (III) below, one of its addition salts, its solvates and/or solvates of its salts:

(III)

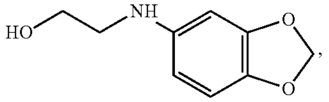

one or more compounds chosen from N,N-dicarboxymethylglutamic acid, its salts and mixtures thereof.

The composition according to the invention, comprising a particular combination of two oxidation couplers and at least one particular acid, makes it possible to achieve the above objectives, in particular in terms of intensity, colour build-up and selectivity of the dyeing of the keratin fibres, and also in terms of the colouring fastness, in particular with respect to shampooing operations.

The present invention also relates to a process for dyeing keratin fibres, in particular human keratin fibres such as the hair, wherein the composition as described previously is applied to said fibres.

The present invention also relates to the use of the composition according to the invention for dyeing keratin fibres, in particular human keratin fibres such as the hair.

The invention furthermore relates to a multicompartment device comprising at least a first compartment containing the composition according to the invention, and at least a second compartment containing one or more oxidizing agents as described hereinafter.

Other subjects, characteristics, aspects and advantages of the invention will emerge even more clearly on reading the description and the example that follows.

In the text which will follow, and unless otherwise indicated, the limits of a range of values are included in this range, in particular in the expressions "of between" and "ranging from . . . to . . . ".

Moreover, the expression "at least one" used in the present description is equivalent to the expression "one or more".

The composition according to the invention comprises at least two particular oxidation couplers.

6-Hydroxybenzomorpholine of Formula (II)

The composition according to the invention comprises an oxidation coupler chosen from 6-hydroxybenzomorpholine of formula (II) below, one of its addition salts, its solvates and/or solvates of its salts:

(II)

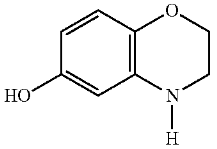

Preferably, the oxidation coupler(s) chosen from 6-hydroxybenzomorpholine of formula (II), one of its addition salts, its solvates and/or solvates of its salts is/are present in a content ranging from 0.001% to 20% by weight, preferably from 0.005% to 15% by weight, more preferentially from 0.01% to 10% by weight, better still from 0.05% to 5%, even better still from 0.1% to 3% by weight, relative to the weight of the composition.

Hydroxyethyl-3,4-methylenedioxyaniline of Formula (III)

The composition according to the invention also comprises at least one oxidation coupler chosen from hydroxyethyl-3,4-methylenedioxyaniline of formula (III) below, one of its addition salts, its solvates and/or solvates of its salts:

(III)

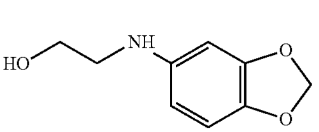

Preferably, the oxidation coupler(s) chosen from hydroxyethyl-3,4-methylenedioxyaniline of formula (III), one of its addition salts, its solvates and/or solvates of its salts is/are present in a total content ranging from 0.001% to 20% by weight, preferably from 0.005% to 15% by weight, more preferentially from 0.01% to 10% by weight, better still from 0.05% to 5%, even better still from 0.1% to 3% by weight, relative to the total weight of the composition.

Advantageously, the oxidation coupler(s) chosen from 6-hydroxybenzomorpholine of formula (II), one of its addition salts, its solvates and/or solvates of its salts is/are present in a content ranging from 0.001% to 20% by weight, preferably from 0.005% to 15% by weight, more preferentially from 0.01% to 10% by weight, better still from 0.05% to 5%, even better still from 0.1% to 3% by weight, relative to the weight of the composition, and the oxidation coupler(s) chosen from hydroxyethyl-3,4-methylenedioxyaniline of formula (ITT), one of its addition salts, its solvates and/or solvates of its salts is/are present in a total content ranging from 0.001% to 20% by weight, preferably from 0.005% to 15% by weight, more preferentially from 0.01% to 10% by weight, better still from 0.05% to 5%, even better still from 0.1% to 3% by weight, relative to the total weight of the composition.

Advantageously, the total content of oxidation couplers chosen from 6-hydroxybenzomorpholine of formula (I), its addition salts, its solvates and/or solvates of its salts, and hydroxyethyl-3,4-methylenedioxyaniline of formula (ITT), its addition salts, its solvates and/or solvates of its salts, ranges from 0.001% to 20% by weight, preferably from 0.005% to 15% by weight, more preferentially from 0.01% to 10% by weight, better still from 0.05% to 5%, even better still from 0.1% to 3% by weight, relative to the total weight of the composition.

Advantageously, the weight ratio between the content of oxidation couplers chosen from 6-hydroxybenzomorpholine of formula (II) and the content of oxidation couplers chosen from hydroxyethyl-3,4-methylenedioxyaniline of formula (III), their addition salts, their solvates and/or the solvates of their salts is between 0.1 and 10, preferably between 0.4 and 5, more preferentially between 0.5 and 2.

Additional Oxidation Couplers

The composition according to the invention may optionally additionally comprise one or more oxidation couplers different from 6-hydroxybenzomorpholine of formula (II), hydroxyethyl-3,4-methylenedioxyaniline of formula (III), their addition salts, their solvates and/or the solvates of their salts.

These oxidation couplers are referred to herein as additional oxidation couplers.

By way of example, the additional oxidation couplers may be chosen from meta-phenylenediamines, meta-aminophenols, meta-diphenols, naphthalene-based coupling agents, and heterocyclic coupling agents, and their corresponding addition salts, their solvates and/or the solvates of their salts according to the invention.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, α-naphthol, 2-methyl-1-naphthol, 6-hydroxyindole, 4-hydroxyindole, 4-hydroxy-N-methylindole, 2-amino-3-hydroxypyridine, 3,5-diamino-2,6-dimethoxypyridine, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b][1,2,4]triazole, 2,6-dimethyl[3,2-c][1,2,4]triazole and 6-methylpyrazolo[1,5-a]benzimidazole, 2-methyl-5-aminophenol, 2-amino-5-ethylphenol, 5-N-(β-hydroxyethyl)amino-2-methylphenol, 3-aminophenol, 3-amino-2-chloro-6-methylphenol, 2-([3-amino-4-methoxyphenyl]amino)ethanol, the corresponding addition salts with an acid, the solvates and/or the solvates of the salts.

According to a preferred embodiment of the invention, the additional oxidation coupler(s) is/are chosen from meta-phenylenediamines, meta-aminophenols, meta-diphenols, naphthalene-based coupling agents, heterocyclic coupling agents, and their corresponding addition salts, their solvates and/or the solvates of their salts; even more preferentially 1,3-dihydroxybenzene, 1,3-dihydroxy-2-methylbenzene, 3-aminophenol, 5-N-(β-hydroxyethyl)amino-2-methylphenol, 2,4-diamino-1-(β-hydroxyethyloxy)benzene, 2-methyl-5-aminophenol, 2-amino-5-ethylphenol, 6-hydroxyindole, 4-chloro-1,3-dihydroxybenzene, 2-amino-3-hydroxypyridine, 3-amino-2-chloro-6-methylphenol, α-naphthol, 2-([3-amino-4-methoxyphenyl]amino)ethanol and their addition salts, their solvates and/or the solvates of their salts.

In a particular embodiment, the composition according to the invention is free from oxidation couplers chosen from resorcinol, 2-methylresorcinol, 4-chlororesorcinol, their addition salts, their solvates and the solvates of their salts.

Preferably, when they are present, the total content of additional oxidation couplers different from the couplers of formulae (II) and (III), their salts, their solvates and/or solvates of their salts ranges from 0.001% to 20% by weight, preferably from 0.005% to 15% by weight, more preferentially from 0.01% to 10% by weight, better still from 0.05% to 5%, even better still from 0.1% to 3% by weight, relative to the weight of the composition.

Preferably, the total content of oxidation couplers, their salts, their solvates and/or solvates of their salts ranges from 0.001% to 20% by weight, preferably from 0.005% to 15% by weight, more preferentially from 0.01% to 10% by weight, better still from 0.05% to 5%, even better still from 0.1% to 3% by weight, relative to the weight of the composition.

N,N-Dicarboxymethylglutamic acid, its Salts

The composition according to the invention also comprises one or more compounds chosen from N,N-dicarboxymethylglutamic acid, its salts and mixtures thereof.

The salts are in particular alkali metal, alkaline-earth metal, ammonium and substituted ammonium salts.

Among the salts of these compounds, the alkali metal salts and especially the sodium or potassium salts are preferred.

The composition according to the invention preferably comprises tetrasodium glutamate diacetate (GLDA). Use will for example be made of Dissolvine GL38 or 45S from Akzo Nobel.

Preferably, the total content of the compound(s) chosen from N,N-dicarboxymethylglutamic acid, its salts and mixtures thereof ranges from 0.001% to 15% by weight, more preferentially from 0.005% to 10% by weight, better still from 0.01% to 8% by weight, even better still from 0.05% to 5% by weight, or even from 0.075% to 2% by weight, relative to the total weight of the composition.

According to a preferred embodiment, the total content of tetrasodium glutamate diacetate (GLDA) ranges from 0.001% to 15% by weight, more preferentially from 0.005% to 10% by weight, better still from 0.01% to 8% by weight, even better still from 0.05% to 5% by weight, or even from 0.075% to 2% by weight, relative to the total weight of the composition.

Oxidation Bases

The composition according to the invention may optionally also comprise one or more oxidation bases.

Preferably, the composition according to the invention additionally comprises one or more oxidation bases.

By way of example, the oxidation bases are chosen from para-phenylenediamines, bis(phenyl)alkylenediamines, para-aminophenols, ortho-aminophenols, heterocyclic bases and the corresponding addition salts, solvates and solvates of their salts.

Among the para-phenylenediamines that may be mentioned are, for example, para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-(γ-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the corresponding addition salts with an acid, the solvates and/or the solvates of their salts.

Among the para-phenylenediamines mentioned above, particular preference is given to para-phenylenediamine, para-toluenediamine, 2-isopropyl-para-phenylenediamine, 2-β-hydroxyethyl-para-phenylenediamine, 2-(γ-hydroxypropyl)-para-phenylenediamine, 2-methoxymethyl-para-phenylenediamine, 2-$-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the corresponding addition salts with an acid, the solvates and/or the solvates of their salts.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the corresponding addition salts, the solvates and/or the solvates of their salts.

Among the para-aminophenols that are mentioned are, for example, para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the corresponding addition salts with an acid, the solvates and/or the solvates of their salts.

Among the ortho-aminophenols that may be mentioned, for example, are 2-aminophenol, 2-amino-5-methylphenol, 2-amino-6-methylphenol and 5-acetamido-2-aminophenol, and the corresponding addition salts, the solvates and/or the solvates of their salts.

Among the heterocyclic bases that may be mentioned, for example, are pyridine, pyrimidine and pyrazole derivatives.

Among the pyridine derivatives that may be mentioned are the compounds described, for example, in patents GB 1 026 978 and GB 1 153 196, for example 2,5-diaminopyridine, 2-(4-methoxyphenyl)amino-3-aminopyridine and 3,4-diaminopyridine, and the corresponding addition salts, the solvates and/or the solvates of their salts.

Other pyridine oxidation bases that are useful in the present invention are the 3-aminopyrazolo[1,5-a]pyridine oxidation bases or the corresponding addition salts described, for example, in patent application FR 2 801 308. Examples that may be mentioned include pyrazolo[1,5-a]pyrid-3-ylamine, 2-acetylaminopyrazole[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazole[1,5-a]pyridine, 3,4-diaminopyrazole[1,5-a]pyridine, pyrazolo[1,5-a]pyridine-3), 7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-β-hydroxyethoxy-3-aminopyrazolo[1,5-a]pyridine and 2-(4-dimethylpiperazinium-1-yl)-3-aminopyrazolo[1,5-a]pyridine, and the corresponding addition salts, the solvates and/or the solvates of their salts.

More particularly, the oxidation bases that are useful in the present invention are chosen from 3-aminopyrazolo[1,5-a]pyridines and preferably substituted on carbon atom 2 with:

a) a (di)(C1-C6)(alkyl)amidino group, said alkyl group possibly being substituted with at least one hydroxyl, amino or imidazolium group;

b) an optionally cationic 5- to 7-membered heterocycloalkyl group comprising from 1 to 3 heteroatoms, optionally substituted with one or more (C1-C6)alkyl groups such as a di(C1-C4)alkylpiperazinium group; or c) a (C1-C6)alkoxy group optionally substituted by one or more hydroxyl groups, such as a O-hydroxyalkoxy group, and the corresponding addition salts, the solvates and/or the solvates of their salts.

The pyrimidine derivatives which may be mentioned include the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the corresponding addition salts. Use may also be made of 4,5-diamino-1-(β-methoxyethyl)pyrazole.

A 4,5-diaminopyrazole will preferably be used and even more preferentially 4,5-diamino-1-(β-hydroxyethyl)pyrazole and/or a corresponding salt, the solvates and/or the solvates of its salts.

The pyrazole derivatives that may also be mentioned comprise diamino-N, N-dihydropyrazolopyrazolones and in particular those described in patent application FR-A-2 886 136, such as the following compounds and the corresponding addition salts: 2,3-diamino-6,7-dihydro-1H,51-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-diiodopyrazole-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one and 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a corresponding salt, solvate and/or solvate of its salts.

Use will preferably be made, as heterocyclic bases, of 4,5-diamino-1-(β-hydroxyethyl)pyrazole and/or 2,3-diamino-6,7-dihydro-1H,5H-pyrazolo[1,2-a]pyrazol-1-one and/or 2-β-hydroxyethoxy-3-aminopyrazolo[1,5-a]pyridine and/or a corresponding salt, solvate and/or solvate of its salts.

Preferably, the oxidation base(s) is/are chosen from para-phenylenediamines, bis(phenyl)alkylenediamines, para-aminophenols, ortho-aminophenols, heterocyclic bases, and the corresponding addition salts, and mixtures thereof; more preferentially from 2-methoxymethyl-para-phenylenediamine, 2-β-hydroxyethyl-para-phenylenediamine, 2-γ-hydroxypropyl-para-phenylenediamine, and their addition salts, their solvates and/or the solvates of their salts and mixtures thereof.

Preferably, when they are present in the composition according to the invention, the oxidation base(s) is/are present in a total content ranging from 0.001% to 20% by weight, preferably from 0.005% to 15% by weight, more preferentially from 0.01% to 10% by weight, better still from 0.05% to 5%, even better still from 0.1% to 3% by weight, relative to the weight of the composition.

Preferably, the composition according to the invention comprises one or more oxidation bases, preferentially chosen from 2-methoxymethyl-para-phenylenediamine, 2-β3-hydroxyethyl-para-phenylenediamine, 2-γ-hydroxypropyl-para-phenylenediamine, and their addition salts, their solvates and/or the solvates of their salts and mixtures thereof.

According to a preferred embodiment, the oxidation base(s) chosen from 2-methoxymethyl-para-phenylenediamine, 2-β-hydroxyethyl-para-phenylenediamine, 2-γ-hydroxypropyl-para-phenylenediamine, their addition salts, their solvates and/or the solvates of their salts and mixtures thereof is/are present in a total content ranging from 0.001% to 20% by weight, preferably from 0.005% to 15% by weight, more preferentially from 0.01% to 10% by weight, better still from 0.05% to 5%, even better still from 0.1% to 3% by weight, relative to the weight of the composition.

In a particular embodiment, the composition according to the invention is free from oxidation bases chosen from para-phenylenediamine, para-toluenediamine, their addition salts, their solvates and the solvates of their salts.

Advantageously, the weight ratio between the total content of oxidation base(s) and the total content of oxidation coupler chosen from 6-hydroxybenzomorpholine of formula (II), hydroxyethyl-3,4-methylenedioxyaniline of formula (III), one of their addition salts, their solvates and/or the solvates of their salts is between 0.1 and 10, better still between 0.5 and 5.

Advantageously, the weight ratio between the total content of oxidation base(s) and the total content of couplers is between 0.1 and 10, better still between 0.5 and 5.

Fatty Substance

The composition according to the invention may comprise one or more fatty substances.

Useful fatty substances according to the invention may be liquid fatty substances (or oils) and/or solid fatty substances. A liquid fatty substance is understood to be a fatty substance having a melting point of less than or equal to 25° C. at atmospheric pressure ($1.013\times10^5$ Pa). A solid fatty substance is understood to be a fatty substance having a melting point of greater than 25° C. at atmospheric pressure ($1.013\times10^5$ Pa).

For the purposes of the present invention, the melting point corresponds to the temperature of the most endothermic peak observed on thermal analysis (differential scanning calorimetry or DSC) as described in the standard ISO 11357-3; 1999. The melting point may be measured using a differential scanning calorimeter (DSC), for example the calorimeter sold under the name "MDSC 2920" by the company TA Instruments. In the present patent application, all the melting points are determined at atmospheric pressure ($1.013\times10^5$ Pa).

The term "fatty substance" is understood to mean an organic compound that is insoluble in water at 25° C. and at atmospheric pressure ($1.013\times10^5$ Pa) (solubility of less than 5% by weight, and preferably less than 1% by weight, even more preferentially less than 0.1% by weight). They bear in their structure at least one hydrocarbon-based chain including at least 6 carbon atoms and/or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

Advantageously, the fatty substances that may be used in the present invention are neither (poly)oxyalkylenated nor (poly)glycerolated.

Preferably, useful fatty substances according to the invention are non-silicone.

The term "non-silicone fatty substance" is intended to mean a fatty substance not containing any Si—0 bonds and the term "silicone fatly substance" is intended to mean a fatty substance containing at least one Si—0 bond.

More particularly, the liquid fatty substance(s) according to the invention is/are chosen from C6 to C16 liquid hydrocarbons, liquid hydrocarbons comprising more than 16 carbon atoms, non-silicone oils of animal origin, oils of triglyceride type of plant or synthetic origin, fluoro oils, liquid fatty alcohols, liquid esters of a fatty acid and/or of a fatty alcohol other than triglycerides, and silicone oils, and mixtures thereof.

It is recalled that the fatty alcohols, esters and acids more particularly contain at least one saturated or unsaturated, linear or branched hydrocarbon-based group, comprising from 6 to 40 and better still from 8 to 30 carbon atoms, which is optionally substituted, in particular, with one or more hydroxyl groups (in particular 1 to 4). If they are unsaturated, these compounds may comprise one to three conjugated or unconjugated carbon-carbon double bonds.

As regards the C6 to C16 liquid hydrocarbons, these may be linear, branched, or optionally cyclic, and are preferably chosen from alkanes. Examples that may be mentioned include hexane, cyclohexane, undecane, dodecane, isododecane, tridecane or isoparaffins, such as isohexadecane or isodecane, and mixtures thereof.

The liquid hydrocarbons comprising more than 16 carbon atoms may be linear or branched, and of mineral or synthetic origin, and are preferably chosen from liquid paraffins or liquid petroleum jelly, polydecenes, hydrogenated polyisobutene such as Parleam®, and mixtures thereof.

A hydrocarbon-based oil of animal origin that may be mentioned is perhydrosqualene.

The triglyceride oils of plant or synthetic origin are preferably chosen from liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names Miglyol® a 810, 812 and 818 by the company Dynamit Nobel, jojoba oil and shea butter oil, and mixtures thereof.

As regards the fluoro oils, they may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethylpertluoromorpholine sold under the name PF 5052® by the company 3M.

The liquid fatty alcohols that are suitable for use in the invention are more particularly chosen from linear or branched, saturated or unsaturated alcohols, preferably unsaturated or branched alcohols, comprising from 6 to 40 carbon atoms, preferably from 8 to 30 carbon atoms. Examples that may be mentioned include octyldodecanol, 2-butyloctanol, 2-hexyldecanol, 2-undecylpentadecanol, isostearyl alcohol, oleyl alcohol, linolenyl alcohol, ricinoleyl alcohol, undecylenyl alcohol and linoleyl alcohol, and mixtures thereof.

As regards the liquid esters of fatty acids and/or of fatty alcohols, other than the triglycerides mentioned previously, mention may be made notably of esters of saturated or unsaturated, linear C1 to C26 or branched C3 to C26 aliphatic mono- or polyacids and of saturated or unsaturated, linear C1 to C26 or branched C3 to C26 aliphatic mono- or polyalcohols, the total carbon number of the esters being greater than or equal to 6 and more advantageously greater than or equal to 10.

Preferably, for the esters of monoalcohols, at least one from among the alcohol and the acid from which the esters of the invention are derived is branched.

Among the monoesters, mention may be made of dihydroabietyl behenate; octyldodecyl behenate; isocetyl behenate; isostearyl lactate; lauryl lactate; linoleyl lactate; oleyl lactate; isostearyl octanoate; isocetyl octanoate; octyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; octyl isononanoate; 2-ethylhexyl isononanoate; octyldodecyl erucate: oleyl erucate; ethyl palmitate, isopropyl palmitate, such as 2-ethylhexyl palmitate, 2-octyldecyl palmitate; alkyl myristates such as isopropyl myristate, isobutyl stearate; 2-hexyldecyl laurate, and mixtures thereof.

Preferably, among the monoesters of monoacids and of monoalcohols, use will be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate, and mixtures thereof.

Still within the context of this variant, esters of C4 to C22 dicarboxylic or tricarboxylic acids and of C1 to C22 alcohols and esters of monocarboxylic, dicarboxylic or tricarboxylic acids and of C2 to C26 dihydroxy, trihydroxy, tetrahydroxy or pentahydroxy alcohols may also be used.

Mention may in particular be made of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; polyethylene glycol distearates, and mixtures thereof.

The composition may also comprise, as fatty ester, sugar esters and diesters of C6 to C30 and preferably C12 to C22 fatty acids. It is recalled that the term "sugar" is intended to mean oxygen-bearing hydrocarbon-based compounds bearing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose, glucose, galactose, ribose, fucose, maltose, fructose, mannose, arabinose, xylose and lactose, and derivatives thereof, notably alkyl derivatives, such as methyl derivatives, for instance methylglucose.

The sugar esters of fatty acids may be notably chosen from the group comprising the esters or mixtures of esters of sugars described previously and of linear or branched, saturated or unsaturated C6 to C30 and preferably C12 to C22 fatty acids. If they are unsaturated, these compounds may comprise one to three conjugated or unconjugated carbon-carbon double bonds.

The esters according to this variant may also be chosen from mono-, di-, tri- and tetraesters, polyesters, and mixtures thereof.

These esters may be, for example, oleates, laurates, palmitates, myristates, behenates, cocoates, stearates, linoleates, linolenates, caprates, arachidonates or mixtures thereof notably such as the mixed oleo-paimitate, oleo-stearate and palmito-stearate esters.

More particularly, use is made of monoesters and diesters and notably sucrose, glucose or methylglucose mono- or dioleates, -stearates, -behenates, -oleopalimitates, -linoleates, -linolenates and -oleostearates, and mixtures thereof.

An example that may be mentioned is the product sold under the name Glucate® DO by the company Amerchol, which is a methylglucose dioleate.

Preferably, use will be made of a liquid ester of a monoacid and of a monoalcohol.

The silicone oils that may be used in the composition according to the present invention may be volatile or non-volatile, cyclic, linear or branched silicone oils, which are unmodified or modified with organic groups, and preferably have a viscosity from $5\times10^{-6}$ to 2.5 $m^2/s$ at 25° C., and preferably $1\times10^{-5}$ $m^2/s$.

Preferably, the silicone oils are chosen from polydialkylsiloxanes, notably polydimethylsiloxanes (PDMS), and liquid polyorganosiloxanes including at least one aryl group.

These silicone oils may also be organomodified. The organomodified silicone oils that may be used in accordance with the invention are preferably liquid silicones as defined above and including in their structure one or more organofunctional groups attached via a hydrocarbon-based group, chosen, for example, from amine groups and alkoxy groups.

Organopolysiloxanes are defined in greater detail in Walter Noll's *Chemistry and Technology of Silicones* (1968), Academic Press. They may be volatile or nonvolatile.

When they are volatile, the silicone oils are more particularly chosen from those with a boiling point of between 60° C. and 260° C., and even more particularly from:

(i) cyclic polydialkylsiloxanes including from 3 to 7 and preferably from 4 to 5 silicon atoms. These are, for example, octamethylcyclotetrasiloxane notably sold under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide.

Mention may also be made of mixtures of cyclic polydialkylsiloxanes with silicon-based organic compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3' hexatrimethylsilyloxy)neopentane;

(ii) linear volatile polydialkylsiloxanes containing 2 to 9 silicon atoms and having a viscosity of less than or equal to $5\times10^{6}$ $m^2/s$ at 25° C. An example is decamethyltetrasiloxane notably sold under the name SH 200 by the company Toray Silicone. Silicones falling within this category are also described in the article published in Cosmetics and Toiletries, Vol. 91, January 76, pp. 27-32, Todd & Byers, Volatile Silicone Fluids for Cosmetics Nonvolatile polydialkylsiloxanes are preferably used.

These silicone oils are more particularly chosen from polydialkylsiloxanes, among which mention may be made mainly of polydimethylsiloxanes bearing trimethylsilyl end groups. The viscosity of the silicones is measured at 25° C. according to the standard ASTM 445, Appendix C.

Among these polydialkylsiloxanes, mention may be made, in a nonlimiting manner, of the following commercial products:

- the Silbione® oils of the 47 and 70 047 series or the Mirasil® oils sold by Rhodia, for instance the oil 70 047 V 500 000;
- the oils of the Mirasil® series sold by the company Rhodia;
- the oils of the 200 series from the company Dow Corning, such as DC200 with a viscosity of 60 000 $mm^2/s$;
- the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

The organomodified silicones that may be used in accordance with the invention are silicones as defined previously and comprising in their structure one or more organofunctional groups attached via a hydrocarbon-based group.

As regards the liquid polyorganosiloxanes including at least one aryl group, they may notably be polydiphenylsiloxanes, and polyalkylarylsiloxanes functionalized with the organofunctional groups mentioned previously.

The polyalkylarylsiloxanes are particularly chosen from linear and/or branched polydimethyl/methylphenylsiloxanes and polydimethyl/diphenylsiloxanes with a viscosity ranging from $1\times10^{-5}$ to $5\times10^{-2}$ $m^2/s$ at 25° C.

Among these polyalkylarylsiloxanes, examples that may be mentioned include the products sold under the following names:

- the Silbione® oils of the 70 641 series from Rhodia;
- the oils of the Rhodorsil® 70 633 and 763 series from Rhodia;
- the oil Dow Corning 556 Cosmetic Grade Fluid from Dow Corning;
- the silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

Among the organomodified silicones, mention may be made of polyorganosiloxanes including:

- substituted or unsubstituted amino groups, such as the products sold under the names GP 4 Silicone Fluid and GP 7100 by the company Genesee or the products sold under the names Q2 8220 and Dow Corning 929 or 939 by the company Dow Corning. The substituted amino groups are in particular C1 to C4 aminoalkyl groups;
- alkoxy groups,
- hydroxyl groups.

The solid fatty substances according to the invention preferably have a viscosity of greater than 2 Pa·s, measured at 25° C. and at a shear rate of 1 $s^{-1}$.

The solid fatty substance(s) is/are preferably chosen from solid fatty acids, solid fatty alcohols, solid esters of fatty acids and/or of fatty alcohols, waxes, ceramides and mixtures thereof.

The term "fatty acids" is intended to mean a long-chain carboxylic acid comprising from 6 to 40 carbon atoms, preferably from 8 to 30 carbon atoms. The solid fatty acids according to the invention preferentially comprise from 10 to 30 carbon atoms and better still from 14 to 22 carbon atoms. They may possibly be hydroxylated.

These fatty acids are neither oxyalkylenated nor glycerolated.

The solid fatty acids that may be used in the present invention are notably chosen from myristic acid, cetylic acid, stearylic acid, palmitic acid, arachidic acid, stearic acid, lauric acid, behenic acid, 12-hydroxystearic acid, and mixtures thereof.

Particularly preferably, the solid fatty acid(s) is/are chosen from lauric acid, myristic acid, cetylic acid, palmitic acid, and stearic acid.

The term "fatty alcohol" is intended to mean a long-chain aliphatic alcohol comprising from 6 to 40 carbon atoms, preferably from 8 to 30 carbon atoms, and comprising at least one hydroxyl group OH. These fatty alcohols are neither oxyalkylenated nor glycerolated.

The solid fatty alcohols may be saturated or unsaturated, and linear or branched, and include from 8 to 40 carbon atoms, preferably from 10 to 30 carbon atoms. Preferably, the solid fatty alcohols have the structure R—OH with R denoting a linear alkyl group, optionally substituted with one or more hydroxyl groups, comprising from 8 to 40, preferentially from 10 to 30 carbon atoms, better still from 10 to 30, or even from 12 to 24 and even better still from 14 to 22 carbon atoms.

The solid fatty alcohols that may be used are preferably chosen from saturated or unsaturated, linear or branched, preferably linear and saturated, (mono)alcohols including from 8 to 40 carbon atoms, better still from 10 to 30, or even from 12 to 24 and better still from 14 to 22 carbon atoms.

The solid fatty alcohols that may be used may be chosen, alone or as a mixture, from: myristyl alcohol (or 1-tetradecanol); cetyl alcohol (or 1-hexadecanol); stearyl alcohol (or 1-octadecanol); arachidyl alcohol (or 1-eicosanol); behenyl alcohol (or 1-docosanol); lignoceryl alcohol (or 1-tetracosanol); ceryl alcohol (or 1-hexacosanol); montanyl alcohol (or 1-octacosanol); myricyl alcohol (or 1-triacontanol).

Preferentially, the solid fatty alcohol is chosen from cetyl alcohol, stearyl alcohol, behenyl alcohol, myristyl alcohol, arachidyl alcohol, and mixtures thereof, such as cetylstearyl alcohol or cetearyl alcohol. Particularly preferably, the solid fatty alcohol is cetylstearyl or cetearyl alcohol.

The solid esters of a fatty acid and/or of a fatty alcohol that may be used are preferably chosen from esters derived from a C9-C26 carboxylic fatty acid and/or from a C9-C26 fatty alcohol.

Preferably, these solid fatty esters are esters of a linear or branched, saturated carboxylic acid including at least 10 carbon atoms, preferably from 10 to 30 carbon atoms and more particularly from 12 to 24 carbon atoms, and of a linear or branched, saturated monoalcohol, including at least 10 carbon atoms, preferably from 10 to 30 carbon atoms and more particularly from 12 to 24 carbon atoms. The saturated carboxylic acids may be optionally hydroxylated, and are preferably monocarboxylic acids.

Esters of C4-C22 dicarboxylic or tricarboxylic acids and of C1-C22 alcohols and esters of monocarboxylic, dicarboxylic or tricarboxylic acids and of C2-C26 dihydroxylated, trihydroxylated, tetrahydroxylated or pentahydroxylated alcohols may also be used.

Mention may notably be made of octyldodecyl behenate, isocetyl behenate, cetyl lactate, stearyl octanoate, octyl octanoate, cetyl octanoate, decyl oleate, hexyl stearate, octyl stearate, myristyl stearate, cetyl stearate, stearyl stearate, octyl pelargonate, cetyl myristate, myristyl myristate, stearyl myristate, diethyl sebacate, diisopropyl sebacate, diisopropyl adipate, di-n-propyl adipate, dioctyl adipate, dioctyl maleate, octyl palmitate, myristyl palmitate, cetyl palmitate, stearyl palnitate, and mixtures thereof.

Preferably, the solid esters of a fatty acid and/or of a fatty alcohol are chosen from C9-C26 alkyl palmitates, notably myristyl palmitate, cetyl palmitate or stearyl palmitate; C9-C26 alkyl myristates, such as cetyl myristate, stearyl myristate and myristyl myristate; and C9-C26 alkyl stearates, notably myristyl stearate, cetyl stearate and stearyl stearate; and mixtures thereof.

For the purposes of the present invention, a wax is a lipophilic compound, which is solid at 25° C. and atmospheric pressure, with a reversible solid/liquid change of state, having a melting point greater than about 40° C., which may range up to 200° C., and having in the solid state an anisotropic crystal organization. In general, the size of the wax crystals is such that the crystals diffract and/or scatter light, giving the composition that comprises them a more or less opaque cloudy appearance. By bringing the wax to its melting point, it is possible to make it miscible with oils and to form a microscopically homogeneous mixture, but on returning the temperature of the mixture to ambient temperature, recrystallization of the wax, which is microscopically and macroscopically detectable (opalescence), is obtained.

In particular, the waxes that are suitable for use in the invention may be chosen from waxes of animal, plant or mineral origin, non-silicone synthetic waxes, and mixtures thereof.

Mention may be made notably of hydrocarbon-based waxes, for instance beeswax, notably of biological origin, lanolin wax and Chinese insect waxes; rice bran wax, carnauba wax, candelilla wax, ouricury wax, esparto grass wax, berry wax, shellac wax, Japan wax and sumac wax; montan wax, orange wax, lemon wax, microcrystalline waxes, paraffins and ozokerite; polyethylene waxes, the waxes obtained by Fischer-Tropsch synthesis and waxy copolymers, and also esters thereof.

Mention may additionally be made of C20 to C60 microcrystalline waxes, such as Microwax HW.

Mention may also be made of the MW 500 polyethylene wax sold under the reference Permalen 50-L polyethylene.

Mention may also be made of the waxes obtained by catalytic hydrogenation of animal or plant oils containing linear or branched C8-C32 fatty chains. Mention may in particular be made, among these waxes, of isomerized jojoba oil such as trans-isomerized partially hydrogenated jojoba oil, in particular the product manufactured or sold by the company Desert Whale under the commercial reference Iso-Jojoba-50®, hydrogenated sunflower oil, hydrogenated castor oil, hydrogenated coconut oil, hydrogenated lanolin oil and bis(1,1,1-trimethylolpropane) tetrastearate, in particular the product sold under the name Hest 2T-4S® by the company Heterene.

The waxes obtained by hydrogenation of castor oil esterified with cetyl alcohol, such as those sold under the names Phytowax Castor 16L64β and 22L73® by the company Sophim, may also be used.

As wax, use may also be made of a C20-C40 alkyl (hydroxystearyloxy)stearate (the alkyl group comprising from 20 to 40 carbon atoms), alone or as a mixture. Such a wax is notably sold under the names Kester Wax K 82 P®, Hydroxypolyester K 82 P® and Kester Wax K 80 P® by the company Koster Keunen.

It is also possible to use microwaxes in the compositions of the invention; mention may notably be made of carnauba microwaxes, such as the product sold under the name MicroCare 350® by the company Micro Powders, synthetic-wax microwaxes, such as the product sold under the name MicroEase 114S® by the company Micro Powders, microwaxes constituted of a mixture of carnauba wax and polyethylene wax, such as the products sold under the names Micro Care 300® and 310® by the company Micro Powders, microwaxes constituted of a mixture of carnauba wax and of synthetic wax, such as the product sold under the name Micro Care 325® by the company Micro Powders, polyethylene microwaxes, such as the products sold under the names Micropoly 200®, 220®, 220L® and 250S® by the company Micro Powders, and polytetrafluoroethylene microwaxes, such as the products sold under the names Microslip 519® and 519 L® by the company Micro Powders.

The waxes are preferably chosen from mineral waxes, for instance paraffin, petroleum jelly, lignite or ozokerite wax; plant waxes, for instance cocoa butter or cork fibre or sugar cane waxes, olive tree wax, rice wax, hydrogenated jojoba wax, ouricury wax, carnauba wax, candelilla wax, esparto grass wax, or absolute waxes of flowers, such as the blackcurrant blossom essential wax sold by the company Bertin (France); waxes of animal origin, for instance beeswaxes or modified beeswaxes (cera bellina), spermaceti, lanolin wax and lanolin derivatives; microcrystalline waxes; and mixtures thereof.

The ceramides, or ceramide analogues such as glycoceramides, that may be used in the compositions according to the invention, are known; mention may in particular be made of ceramides of classes T, II, III and V according to the Dawning classification.

The ceramides or analogues thereof that may be used preferably correspond to the following formula: $R^3CH(OH)CH(CH_2OR_2)(NHCOR^1)$, in which:

- $R^1$ denotes a linear or branched, saturated or unsaturated alkyl group, derived from C14-C30 fatty acids, it being possible for this group to be substituted with a hydroxyl group in the alpha position, or a hydroxyl group in the omega position esterified with a saturated or unsaturated C16-C30 fatty acid;
- $R^2$ denotes a hydrogen atom, a (glycosyl)n group, a (galactosyl)m group or a sulfogalactosyl group, in which n is an integer ranging from 1 to 4 and m is an integer ranging from 1 to 8;
- $R^3$ denotes a C15-C26 hydrocarbon-based group, saturated or unsaturated in the alpha position, it being possible for this group to be substituted with one or more C1-C14 alkyl groups; it being understood that in the case of natural ceramides or glycoceramides, $R^3$ may also denote a C15-C26 alpha-hydroxyalkyl group, the hydroxyl group being optionally esterified by a C16-C30 alpha-hydroxy acid.

The ceramides that are more particularly preferred are the compounds for which $R^1$ denotes a saturated or unsaturated alkyl derived from C16-C22 fatty acids; $R^2$ denotes a hydrogen atom and $R^3$ denotes a saturated linear C15 group.

Preferentially, use is made of ceramides for which $R^1$ denotes a saturated or unsaturated alkyl group derived from C14-C30 fatty acids; $R^2$ denotes a galactosyl or sulfogalactosyl group; and $R^3$ denotes a $-CH{=}CH-(CH_2)_{12}-CH_3$ group.

Use may also be made of the compounds for which $R^1$ denotes a saturated or unsaturated alkyl radical derived from C12-C22 fatty acids; $R^2$ denotes a galactosyl or sulfogalactosyl radical and $R^3$ denotes a saturated or unsaturated C12-C22 hydrocarbon-based radical and preferably a $-CH{=}CH(CH_2)_{12}-CH_3$ group.

As compounds that are particularly preferred, mention may also be made of 2-N-linoleoylaminooctadecane-1,3-diol; 2-N-oleoylaminooctadecane-1,3-diol; 2-N-palmitoylaminooctadecane-1,3-diol; 2-N-stearoylaminooctadecane-1,3-diol; 2-N-behenoylaninooctadecane-1,3-diol; 2-N-[2-hydroxypalmitoyl]aminooctadecane-1,3-diol; 2-N-stearoylaminooctadecane-1,3,4-triol and in particular N-stearoylphytosphingosine; 2-N-palmitoylaminohexadecane-1,3-diol, N-linoleoyldihydrosphingosine, N-oleoyidihydrosphingosine, N-palmitoyldihydrosphingosine, N-stearoyldihydrosphingosine, and N-behenoyldihydrosphingosine, N-docosanoyl-N-methyl-D-glucamine, cetylic acid N-(2-hydroxyethyl)-N-(3-cetyloxy-2-hydroxypropyl)amide and bis(N-hydroxyethyl-N-cetyl)malonamide; and mixtures thereof. N-Oleoyldihydrosphingosine will preferably be used.

The solid fatty substances are preferably chosen from solid fatty acids, solid fatty alcohols and mixtures thereof.

According to a preferred embodiment, the composition according to the invention comprises at least one liquid fatty substance, preferentially chosen from liquid hydrocarbons containing more than 16 carbon atoms, plant oils, liquid fatty alcohols and liquid fatty esters, silicone oils and mixtures thereof.

Preferentially, the liquid fatty substance(s) is/are chosen from liquid hydrocarbons comprising more than 16 carbon atoms, in particular liquid petroleum jelly, liquid fatty alcohols, and mixtures thereof.

According to another preferred embodiment, the composition according to the invention comprises at least one solid fatty substance, preferentially chosen from solid fatty alcohols.

According to another preferred embodiment, the composition according to the invention comprises at least one liquid fatty substance and at least one solid fatty substance, preferentially at least one liquid fatty alcohol and at least one solid fatty alcohol.

When the composition according to the invention comprises one or more fatty substances, the total content of fatty substance(s) preferably ranges from 5% to 80% by weight, more preferentially from 8% to 70% by weight and better still from 10% to 65% by weight, relative to the total weight of the composition.

In a particular embodiment, the composition according to the invention comprises one or more fatty substances, the total content of fatty substance(s) preferably ranging from 30% to 80% by weight, more preferentially from 35% to 70% by weight and better still from 40% to 65% by weight, relative to the total weight of the composition.

In another particular embodiment, the composition according to the invention comprises one or more liquid fatty substances, the total content of liquid fatty substance(s) preferably ranging from 30% to 80% by weight, more preferentially from 35% to 70% by weight and better still from 40% to 65% by weight, relative to the total weight of the composition.

Surfactants

The composition according to the present invention may comprise one or more surfactants. These may be chosen preferably from anionic surfactants, nonionic surfactants and cationic surfactants and/or mixtures thereof.

The term "anionic surfactant" is understood to mean a surfactant including, as ionic or ionizable groups, only anionic groups. These anionic groups are preferably chosen from the groups $CO_2H$, $CO_2$—, $SO_3$, $SO_3$—, $OSO_3H$—, OSO3-, $H_2PO_3$, HPO3-, $PO_3$2-, $H_2PO_2$, HPO2-, $PO_2$2-, POH and PO—.

As examples of anionic surfactants that can be used in the composition according to the invention, mention may be made of alkyl sulfates, alkyl ether sulfates, alkylamido ether sulfates, alkylaryl polyether sulfates, monoglyceride sulfates, alkylsulfonates, alkylamidesulfonates, alkylarylsulfonates, α-olefinsulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N—(C1-C4)alkyl N-acyltaurates, salts of alkyl monoesters and of polyglycoside-polycarboxylic acids, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds (unless specified otherwise) generally comprising from 6 to 24 carbon atoms and the aryl group generally denoting a phenyl group.

These compounds may be oxyethylenated and then preferably comprise from 1 to 50 ethylene oxide units.

The salts of C6-C24 alkyl monoesters and of polyglycoside-polycarboxylic acids may be chosen from C6-C24 alkyl polyglycoside-citrates, C6-C24 alkyl polyglycoside-tartrates and C6-C24 alkyl polyglycoside-sulfosuccinates.

When the anionic surfactant(s) is/are in salt form, it/they may be chosen from alkali metal salts such as the sodium or potassium salt and preferably the sodium salt, ammonium salts, amine salts and in particular amino alcohol salts or alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts and in particular the sodium or magnesium salts are preferably used.

The anionic surfactants that are optionally present may be mild anionic surfactants, i.e. anionic surfactants without a sulfate function.

As regards mild anionic surfactants, mention may be made in particular of the following compounds and salts thereof, and also mixtures thereof: polyoxyalkylenated alkyl ether carboxylic acids, polyoxyalkylenated alkylaryl ether carboxylic acids, polyoxyalkylenated alkylamido ether carboxylic acids, in particular those comprising 2 to 50 ethylene oxide groups, alkyl D-galactoside uronic acids, acyl sarcosinates, acyl glutamates and alkylpolyglycoside carboxylic esters.

Use may be made very particularly of polyoxyalkylenated alkyl ether carboxylic acids, for instance lauryl ether carboxylic acid (4.5 EO) sold, for example, under the name Akypo RLM 45 CA from Kao.

Among the anionic surfactants mentioned above, use is preferably made of the sulfated surfactants such as the alkyl sulfates or alkyl ether sulfates, and the acyl glutamates, more preferentially the alkyl sulfates.

The nonionic surfactant(s) that may be used in the composition of the present invention are in particular described, for example, in the *Handbook of Surfactants* by M. R. Porter, published by Blackie &. Son (Glasgow and London), 1991, pp 116-178.

Examples of nonionic surfactants that may be mentioned include the following compounds, alone or as a mixture:

- oxyalkylenated (C8-C24)alkylphenols;
- saturated or unsaturated, linear or branched, oxyalkylenated or glycerolated C8-C40 alcohols, preferably comprising one or two fatty chains;
- saturated or unsaturated, linear or branched, oxyalkylenated C8 to C30 fatty acid amides;
- esters of saturated or unsaturated, linear or branched, C8 to C30 acids and of polyethylene glycols;
- preferably oxyethylenated esters of saturated or unsaturated, linear or branched, C8 to C30 acids and of sorbitol;
- esters of fatty acids and of sucrose;
- C8-C30 fatty acid esters of sorbitan,
- oxyethylenated C8-C30 fatty acid esters of sorbitan,
- (C8-C30)alkyl(poly)glucosides and (C8-C30)alkenyl (poly)glucosides, which are optionally oxyalkylenated (0 to 10 oxyalkylene units) and comprise from 1 to 15 glucose units, (C8-C30)alkyl(poly)glucoside esters;

saturated or unsaturated oxyethylenated plant oils;

condensates of ethylene oxide and/or of propylene oxide;

N—(C8-C30)alkylglucamine and N—(C8-C30)acylmethylglucamine derivatives;

amine oxides.

They are notably chosen from alcohols, α-diols and (C1-C20)alkylphenols, these compounds being ethoxylated, propoxylated or glycerolated and bearing at least one fatty chain comprising, for example, from 8 to 24 carbon atoms, preferably from 8 to 18 carbon atoms, the number of ethylene oxide or propylene oxide groups possibly ranging notably from 1 to 200, and the number of glycerol groups possibly ranging notably from 1 to 30.

Mention may also be made of condensates of ethylene oxide and of propylene oxide with fatty alcohols, ethoxylated fatty amides preferably containing from 1 to 30 ethylene oxide units, polyglycerolated fatty amides comprising on average from 1 to 5, and in particular from 1.5 to 4, glycerol groups, ethoxylated fatty acid esters of sorbitan containing from 1 to 30 ethylene oxide units, fatty acid esters of sucrose, fatty acid esters of polyethylene glycol, (C6-C24 alkyl)polyglycosides, oxyethylenated plant oils, N—(C6-C24 alkyl)glucamine derivatives, amine oxides such as (C10-C14 alkyl)amine oxides or N—(C10-C14 acyl)aminopropylmorpholine oxides.

The C8-C30, preferably C12-C22, fatty acid esters (especially monoesters, diesters and triesters) of sorbitan may be chosen from:

sorbitan caprylate; sorbitan cocoate; sorbitan isostearate; sorbitan laurate; sorbitan oleate; sorbitan palmitate; sorbitan stearate; sorbitan diisostearate; sorbitan dioleate; sorbitan distearate; sorbitan sesquicaprylate; sorbitan sesquiisostearate; sorbitan sesquioleate; sorbitan sesquistearate; sorbitan triisostearate; sorbitan trioleate; sorbitan tristearate.

The polyoxyethylenated C8-C30 (preferably C112-C18) fatty acid esters (especially monoesters, diesters and triesters) of sorbitan especially containing from 2 to 20 mol of ethylene oxide may be chosen from polyoxyethylenated esters of C12-C18 fatty acids, in particular lauric, myristic, cetylic or stearic acid, and of sorbitan especially containing from 2 to 30 mol of ethylene oxide, such as:

polyoxyethylenated sorbitan monolaurate (4 EO) (POLYSORBATE-21), polyoxyethylenated sorbitan monolaurate (20 EO) (POLYSORBATE-20), polyoxyethylenated sorbitan monopalmitate (20 EO) (POLYSORBATE-40), polyoxyethylenated sorbitan monostearate (20 EO) (POLYSORBATE-60), polyoxyethylenated sorbitan monostearate (4 EO) (POLYSORBATE-61), polyoxyethylenated sorbitan monooleate (20 EO) (POLYSORBATE-80), polyoxyethylenated sorbitan monooleate (5 EO) (POLYSORBATE-81).

polyoxyethylenated sorbitan tristearate (20 EO) (POLYSORBA TE-65), polyoxyethylenated sorbitan trioleate (20 EO) (POLYSORBATE-85).

The polyoxyethylenated C8-C30 (preferably C12-C18) fatty acid esters (especially monoesters, diesters, triesters and tetraesters) of sorbitan, especially containing from 2 to 20 mol of ethylene oxide, may be chosen from polyoxyethylenated esters, especially containing from 2 to 20 mol of ethylene oxide, such as of C12-C18 fatty acids, in particular lauric, myristic, cetylic or stearic acid, and of sorbitan, such as:

the ester polyoxyethylenated with 20 EO of sorbitan and of cocoic acid (PEG-20 Sorbitan Cocoate);

the polyoxyethylenated esters (especially containing from 2 to 20 EO) of sorbitan and of isostearic acid (such as PEG-2 Sorbitan Isostearate; PEG-5 Sorbitan Isostearate; PEG-20 Sorbitan Isostearate such as the product sold under the name Nikkol TI 10 V by the company Nikkol), the polyoxyethylenated esters (especially containing from 2 to 20 EO) of sorbitan and of lauric acid (such as PEG-10 Sorbitan Laurate), the polyoxyethylenated esters (especially containing from 2 to 20 EO) of sorbitan and of oleic acid containing 10 oxyethylene groups (such as PEG-6 Sorbitan Oleate; PEG-20 sorbitan oleate), the polyoxyethylenated esters (especially containing from 3 to 20 EO) of sorbitan and of stearic acid (such as PEG-3 Sorbitan Stearate; PEG-4 Sorbitan Stearate; PEG-6 Sorbitan Stearate).

The nonionic surfactants are preferably chosen from ethoxylated C8-C24 fatty alcohols comprising from 1 to 200 ethylene oxide groups, ethoxylated C8-C30 fatty acid esters of sorbitan having from 1 to 30 ethylene oxide units, (C6-C24 alkyl)polyglycosides and mixtures thereof.

The cationic surfactant(s) that may be used in the composition according to the invention are generally chosen from optionally polyoxyalkylenated primary, secondary or tertiary fatty amines, quaternary ammonium salts, and mixtures thereof.

The fatty amines generally comprise at least one C8-C30 hydrocarbon-based chain. Among the fatty amines that may be used according to the invention, examples that may be mentioned include stearylamidopropyldimethylamine and distearylamine.

Mention may in particular be made, as quaternary ammonium salts, for example, of:

those corresponding to the general formula (X) below:

(X)

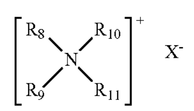

in which the groups $R_8$ to $R_{11}$, which may be identical or different, represent a linear or branched aliphatic group including from 1 to 30 carbon atoms, or an aromatic group such as aryl or alkylaryl, at least one of the groups $R_8$ to $R_{11}$ including from 8 to 30 carbon atoms and preferably from 12 to 24 carbon atoms. The aliphatic groups may include heteroatoms notably such as oxygen, nitrogen, sulfur and halogens.

The aliphatic groups are chosen, for example, from C1-C30 alkyl, C1-C30 alkoxy, polyoxy(C2-C6)alkylene, C1-C30 alkylamide, (C12-C22)alkylamido(C2-C6)alkyl, (C12-C22)alkyl acetate and C1-C30 hydroxyalkyl groups, $X^-$ is an anion chosen from the group of halides, phosphates, acetates, lactates, (C1-C4)alkyl sulfates, (C1-C4)alkylsulfonates or (C1-C4)alkylarylsulfonates.

Among the quaternary ammonium salts of formula (X), preference is given, firstly, to tetraalkylammonium chlorides, for instance dialkyidimethylammoniurn or alkyltrimethylammonium chlorides in which the alkyl group comprises from about 12 to 22 carbon atoms, in particular behenyltrimethylammonium chloride, distearyldimethylammonium chloride, cetyltrimethylammonium chloride or benzyldimethylstearylammonium chloride, or else, secondly, to distearoylethylhydroxyethylmethylammonium methosulfate, dipahnitoylethylhydroxyethylammonium methosulfate or distearoylethylhydroxyethylammonium methosulfate, or else, finally, to palmitylamidopropyltrimethylammonium chloride or stearamidopropyldimethyl(myristyl acetate)ammonium chloride, sold under the name CERAPHYL® 70 by the company Van Dyk;

quaternary ammonium salts of imidazoline, for instance those of formula (XI) below:

(XI)

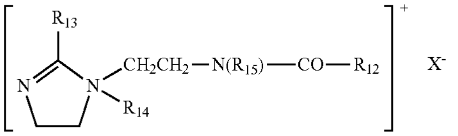

in which $R_{12}$ represents an alkenyl or alkyl group containing from 8 to 30 carbon atoms, derived, for example, from tallow fatty acids, $R_{13}$ represents a hydrogen atom, a C1-C4 alkyl group or an alkenyl or alkyl group containing from 8 to 30 carbon atoms, $R_{14}$ represents a C1-C4 alkyl group, $R_{15}$ represents a hydrogen atom or a C1-C4 alkyl group, $X^-$ is an anion chosen from the group of halides, phosphates, acetates, lactates, (C1-C4)alkyl sulfates, (C1-C4)alkylsulfonates or (C1-C4)alkylarylsulfonates.

Preferably, $R_{12}$ and $R_{13}$ denote a mixture of alkenyl or alkyl groups comprising from 12 to 21 carbon atoms, for example derived from tallow fatty acids, $R_{14}$ denotes a methyl group and $R_{15}$ denotes a hydrogen atom. Such a product is sold, for example, under the name Rewoquat® W 75 by the company Rewo;

quaternary diammonium or triammonium salts, in particular of formula (XII) below:

(XII)

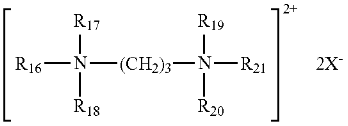

in which $R_{16}$ denotes an alkyl group containing approximately from 16 to 30 carbon atoms, which is optionally hydroxylated and/or interrupted with one or more oxygen atoms; $R^{17}$ is chosen from hydrogen or an alkyl group containing from 1 to 4 carbon atoms or a group $—(CH_2)_3—N+(R_{16a})(R_{17a})(R_{18a})$; $R_{16a}$, $R_{17a}$, $R_{18a}$, $R_{18}$, $R_{19}$, $R_{20}$ and $R_{21}$, which may be identical or different, are chosen from hydrogen or an alkyl group containing from 1 to 4 carbon atoms, and $X^-$ is an anion chosen from the group of halides, acetates, phosphates, nitrates, (C1-C4)alkyl sulfates, (C1-C4)alkylsulfonates or (C1-C4)alkylarylsulfonates, in particular methyl sulfate and ethyl sulfate.

Such compounds are, for example, Finquat CT-P, sold by the company Finetex (Quaternium 89), and Finquat CT, sold by the company Finetex (Quaternium 75);

quaternary ammonium salts containing one or more ester functions, for instance those of formula (XIII) below:

(XIII)

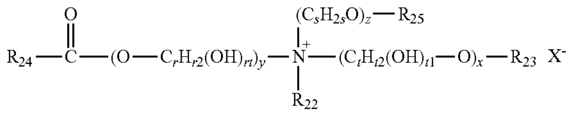

in which: $R_{22}$ is chosen from C1-C6 alkyl groups and C1-C6 hydroxyalkyl or dihydroxyalkyl groups; $R^{23}$ is chosen from: the group $—C(O)R_{26}$, linear or branched, saturated or unsaturated C1-C22 hydrocarbon-based groups $R_{27}$, a hydrogen atom; $R_{25}$ is chosen from: the group $—C(O)R_{28}$, linear or branched, saturated or unsaturated C1-C6 hydrocarbon-based groups $R_{29}$, a hydrogen atom; $R_{24}$, $R_{26}$ and $R_{28}$, which may be identical or different, are chosen from linear or branched, saturated or unsaturated C7-C21 hydrocarbon-based groups; r, s and t, which may be identical or different, are integers from 2 to 6; r1 and t1, which may be identical or different, are 0 or 1; r2+r1=2 r and t1+t2=2 t, y is an integer from 1 to 10, x and z, which may be identical or different, are integers from 0 to 10, $X^-$ is an organic or inorganic simple or complex anion, with the proviso that the sum x+y+z is from 1 to 15, that when x is 0 $R_{23}$ denotes $R_{27}$ and that when z is 0 $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z is from 1 to 10.

When $R_{23}$ is a hydrocarbon-based group $R_{27}$, it may be long and contain from 12 to 22 carbon atoms, or short and contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated C11-C21 hydrocarbon-based groups, and more particularly from linear or branched, saturated or unsaturated C11-C21 alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide, preferably chloride, bromide or iodide, a (C1-C4)alkyl sulfate, (C1-C4)alkylsulfonate or (C1-C4)alkylarylsulfonate. However, use may be made of methanesulfonate, phosphate, nitrate, tosylate, an anion derived from an organic acid, such as acetate or lactate, or any other anion that is compatible with the ammonium bearing an ester function.

The anion $X^-$ is more particularly still chloride, methyl sulfate or ethyl sulfate.

Use is made more particularly, in the composition according to the invention, of the ammonium salts of formula (XIII) in which: $R_{22}$ denotes a methyl or ethyl group, x and y are equal to 1, z is equal to O or 1, r, s and t are equal to 2; $R_{23}$ is chosen from: the group $—C(O)R_{26}$, methyl, ethyl or C14-C22 hydrocarbon-based groups, a hydrogen atom, $R_{25}$ is chosen from: the group —C(O)$R_{28}$, a hydrogen atom, $R_{24}$, $R_{26}$ and $R_{28}$, which may be identical or different, are chosen from linear or branched, saturated or unsaturated C13-C17 hydrocarbon-based groups, and preferably from linear or branched, saturated or unsaturated C13-C17 alkyl and alkenyl groups.

Advantageously, the hydrocarbon-based groups are linear.

Among the compounds of formula (XIII), examples that may be mentioned include salts, notably the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylainmoniium, and mixtures thereof. The acyl groups preferably contain 14 to 18 carbon atoms and are derived more particularly from a plant oil such as palm oil or sunflower oil. When the compound contains several acyl groups, these groups may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably methyl or ethyl halide, a dialkyl sulfate, preferably dimethyl or diethyl sulfate, methyl methanesulfonate, methyl para-toluenesulfonate, glycol chlorohydrin or glycerol chlorohydrin.

Such compounds are sold, for example, under the names Dehyquart® by the company Henkel, Stepanquat® by the company Stepan, Noxamium® by the company CECA or Rewoquat® WE 18 by the company Rewo-Witco.

The composition according to the invention may contain, for example, a mixture of quaternary ammonium monoester, diester and triester salts with a weight majority of diester salts.

Use may also be made of the ammonium salts containing at least one ester function that are described in patents U.S. Pat. Nos. 4,874,554 and 4,137,180.

Use may also be made of the behenoylhydroxypropyltrimethylammonium chloride sold, for example, by the company Kao under the name Quartamin BTC 131.

Preferably, the ammonium salts containing at least one ester function contain two ester functions.

Among the cationic surfactants, it is more particularly preferred to choose cetyltrimethylammonium, behenyltrirmethylammonium and dipalmitoylethylhydroxyethylmethylammonium salts, and mixtures thereof, and more particularly behenyltrimethylammonium chloride, cetyltrimethylammonium chloride, and dipalmitoylethylhydroxyethylammonium methosuilfate, and mixtures thereof.

Preferably, the surfactant(s) is/are chosen from anionic surfactants, nonionic surfactants, and mixtures thereof.

More preferentially, the surfactant(s) is/are preferably chosen from nonionic surfactants, better still from ethoxylated C8-C24 fatty alcohols comprising from 1 to 200 ethylene oxide groups, ethoxylated C8-C30 fatty acid esters of sorbitan having from 1 to 30 ethylene oxide units, (C6-C24 alkyl)polyglycosides, and mixtures thereof.

When the composition comprises one or more surfactants, the total content of surfactant(s) in the composition preferably ranges from 0.01% to 15% by weight, more preferentially from 0.1% to 10% by weight, better still from 0.5% to 8% by weight, even better still from 1% to 6% by weight, relative to the total weight of the composition.

When the composition comprises one or more nonionic surfactants, the total content of nonionic surfactant(s) in the composition preferably ranges from 0.01% to 15% by weight, more preferentially from 0.1% to 10% by weight, better still from 0.5% to 8% by weight, even better still from 1% to 6% by weight, relative to the total weight of the composition.

Sequestrants

The composition according to the invention may comprise at least one sequestrant (or chelating agent) different from N,N-dicarboxymethylglutamic acid and its salts described above.

The definition of a "sequestrant" (or "chelating agent") is well known to those skilled in the art and refers to a compound or a mixture of compounds capable of forming a chelate with a metal ion. A chelate is an inorganic complex in which a compound (the sequestrant or chelating agent) is coordinated to a metal ion, i.e. it forms one or more bonds with the metal ion (formation of a ring including the metal ion).

A sequestrant (or chelating agent) generally comprises at least two electron-donating atoms which enable the formation of bonds with the metal ion.

Within the scope of the present invention, the sequestrant(s) may be chosen from carboxylic acids, preferably aminocarboxylic acids, phosphonic acids, preferably aminophosphonic acids, polyphosphoric acids, preferably linear polyphosphoric acids, their salts, and derivatives thereof.

The salts are in particular alkali metal, alkaline-earth metal, ammonium and substituted ammonium salts.

The following compounds may be mentioned as examples of carboxylic acids: diethylenetriaminepentaacetic acid (DTPA), ethylenediaminedisuccinic acid (EDDS) and trisodium ethylenediamine disuccinate such as Octaquest E30 from OCTEL, ethylenediaminetetraacetic acid (EDTA), and its salts such as disodium EDTA, tetrasodium EDTA, ethylenediamine-N,N'-diglutaric acid (EDDG), glycinamide-N,N'-disuccinic acid (GADS), glycinamide-N,N'-disuccinic acid (GADS), 2-hydroxypropylenediamine-N,N'-disuccinic acid (IPDDS), ethylenediamine-N—N'-bis(ortho-hydroxyphenylacetic acid) (EDDHA), N,N-bis(2-hydroxybenzyl) ethylenediamine-N,N'-diacetic acid (HBED), nitrilotriacetic acid (NTA), methylglycinediacetic acid (MGDA), N-2-hydroxyethyl-N,N-diacetic acid and glyceryliminodiacetic acid (as described in documents EP-A-317,542 and EP-A-399,133), iminodiacetic acid-N-2-hydroxypropylsulfonic acid and aspartic acid-N-carboxymethyl-N-2-hydroxypropyl-3-sulfonic acid (as described in EP-A-516,102), beta-alanine-N,N'-diacetic acid, aspartic acid-N,N'-diacetic acid, aspartic acid-N-monoacetic acid (described in EP-A-509,382), chelating agents based on iminodisuccinic acid (IDSA) (as described in EP-A-509,382), ethanoildiglycine acid, phosphonobutanetricarboxylic acid such as the compound sold by Bayer under the reference Bayhibit AM.

The following compounds may be mentioned as examples of chelating agents based on mono- or polyphosphonic acid: diethylenetriarminepenta(methylenephosphonic acid) (DTPMP), ethane-1-hydroxy-1,1,2-triphosphonic acid (E1HTP), ethane-2-hydroxy-1,1,2-triphosphonic acid (E2HTP), ethane-1-hydroxy-1,1-triphosphonic acid (EHDP), ethane-1,1,2-triphosphonic acid (ETP), ethylenediaminetetrametiylenephosphonic acid (EDTMP), hydroxyethane-1,1-diphosphonic acid (HEDP, etidronic acid), and salts such as disodium etidronate, tetrasodium etidronate.

The following compounds may be mentioned as examples of chelating agents based on polyphosphoric acid: sodium tripolyphosphate (STP), tetrasodium diphosphate, hexametaphosphoric acid, sodium metaphosphate, phytic acid.

According to a particular embodiment, the sequestrant(s) useful according to the invention is/are phosphorus-based sequestrants, i.e. sequestrants which comprise one or more phosphorus atoms, preferably at least two phosphorus atoms.

The phosphorus-based sequestrant(s) used in the composition according to the invention is/are preferably chosen from:

- inorganic phosphorus-based derivatives preferably chosen from alkali metal or alkaline-earth metal, preferably alkali metal, phosphates and pyrophosphates, such as sodium pyrophosphate, potassium pyrophosphate, sodium pyrophosphate decahydrate; and alkali metal or alkaline-earth metal, preferably alkali metal, polyphosphates, such as sodium hexametaphosphate, sodium polyphosphate, sodium tripolyphosphate, sodium trimetaphosphate; which are optionally hydrated, and mixtures thereof;
- organic phosphorus-based derivatives, such as organic (poly)phosphates and (poly)phosphonates, such as etidronic acid and/or alkali metal or alkaline-earth metal salts thereof, for instance tetrasodium etidronate, disodium etidronate and mixtures thereof.

Preferably, the phosphorus-based sequestrant(s) is/are chosen from linear or cyclic compounds comprising at least two phosphorus atoms bonded together covalently via at least one linker L comprising at least one oxygen atom and/or at least one carbon atom.

The phosphorus-based sequestrant(s) may be chosen from inorganic phosphorus-based derivatives, preferably comprising at least two phosphorus atoms. More preferentially, the phosphorus-based sequestrant(s) is/are chosen from alkali metal or alkaline-earth metal pyrophosphates, better still from alkali metal pyrophosphates, in particular sodium pyrophosphate (also known as tetrasodium pyrophosphate).

The phosphorus-based sequestrant(s) may be chosen from organic phosphorus-based derivatives, preferably comprising at least two phosphorus atoms. More preferentially, the phosphorus-based sequestrant(s) is/are chosen from etidronic acid (also known as 1-hydroxyethane-1,1-diphosphonic acid) and/or alkali metal or alkaline-earth metal, preferably alkali metal, salts thereof, for instance tetrasodium etidronate and disodium etidronate.

Thus, preferably, the phosphorus-based sequestrant(s) is/are chosen from alkali metal pyrophosphates, etidronic acid and/or alkali metal salts thereof, and a mixture of these compounds.

Particularly preferably, the phosphorus-based sequestrant(s) is/are chosen from tetrasodium etidronate, disodium etidronate, etidronic acid, tetrasodium pyrophosphate, and a mixture of these compounds.

According to the present invention, the sequestrants are preferably chosen from diethylenetriaminepentaacetic acid (DTPA) and salts thereof, ethylenediaminetetraacetic acid (EDTA) and salts thereof, ethylenediminedisuccinic acid (EDDS) and salts thereof, etidronic acid and salts thereof.

Among the salts of these compounds, the alkali metal salts and especially the sodium or potassium salts are preferred.

When the composition comprises one or more sequestrants different from N,N-dicarboxymethylglutamic acid and salts thereof, the total content thereof preferably ranges from 0.001% to 15% by weight, more preferentially from 0.005% to 10% by weight, better still from 0.01% to 8% by weight, even better still from 0.05% to 5% by weight, relative to the total weight of the composition.

Alkaline Agent

The composition according to the present invention may comprise one or more mineral, organic or hybrid alkaline agents.

Preferably, the composition according to the present invention comprises one or more mineral, organic or hybrid alkaline agents.

For the purposes of the present invention, the terms "alkaline agent" and "basifying agent" are used interchangeably.

The mineral basifying agent(s) is/are preferably chosen from aqueous ammonia, alkali metal carbonates or bicarbonates such as sodium (hydrogen)carbonate and potassium (hydrogen)carbonate, alkali metal or alkaline-earth metal phosphates such as sodium phosphates or potassium phosphates, sodium hydroxides or potassium hydroxides, and mixtures thereof.

The organic basifying agent(s) is/are preferably chosen from alkanolamines, amino acids, organic amines, oxyethylenated and/or oxypropylenated ethylenediamines, 1,3-diaminopropane, 1,3-diamino-2-propanol, spermine or spermidine and mixtures thereof:

The term "alkanolamine" is intended to mean an organic amine comprising a primary, secondary or tertiary amine function, and one or more linear or branched C1-C8 alkyl groups bearing one or more hydroxyl radicals.

Particularly suitable for performing the invention are organic amines chosen from alkanolamines such as monoalkanolamines, dialkanolamines or trialkanolamines comprising one to three identical or different C1-C4 hydroxyalkyl radicals.

In particular, the alkanolamine(s) is/are chosen from monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethyl)aminomethane and mixtures thereof.

Advantageously, the amino acids are basic amino acids comprising an additional amine function. Such basic amino acids are preferably chosen from histidine, lysine, arginine, ornithine and citrulline.

The organic amine can also be chosen from organic amines of heterocyclic type. Besides histidine that has already been mentioned in the amino acids, mention may in particular be made of pyridine, piperidine, imidazole, triazole, tetrazole and benzimidazole. The organic amine can also be chosen from amino acid dipeptides. As amino acid dipeptides that can be used in the present invention, mention may notably be made of carnosine, anserine and balenine. The organic amine may also be chosen from compounds comprising a guanidine function. As amines of this type different from arginine that may be used in the present invention, mention may notably be made of creatine, creatinine, 1,1-dimethylguanidine, 1,1-diethylguanidine, glycocyamine, metformin, agmatine, N-amidoalanine, 3-guanidinopropionic acid, 4-guanidinobutyric acid and 2-([amino(imino)methyl]amino)ethane-1-sulfonic acid.

Use may be made in particular of guanidine carbonate or monoethanolamine hydrochloride as hybrid compounds.

The alkaline agent(s) that may be used according to the invention is/are preferably chosen from alkanolamines such as monoethanolamine, diethanolamine, triethanolamine; aqueous ammonia, carbonates or bicarbonates such as sodium (hydrogen)carbonate and potassium (hydrogen)carbonate and mixtures thereof, more preferentially from aqueous ammonia and alkanolamines, better still from alkanolamines.

When the composition comprises at least one alkaline agent, the total content of the alkaline agent(s) preferably ranges from 0.1% to 40% by weight, more preferentially from 0.5% to 30% by weight, better still from 1% to 20% by weight, even better still from 2% to 10% by weight relative to the total weight of the composition.

According to one embodiment, the pH of the composition comprising at least one alkaline agent is between 8 and 13; preferably between 9 and 12.

The pH of the composition may be adjusted to the desired value by means of acidic or alkaline agent(s) commonly used in the dyeing of keratin fibres, such as those described hereinabove, or alternatively using buffer systems known to those skilled in the art.

Chemical Oxidizing Agents

The composition according to the invention may optionally additionally comprise one or more chemical oxidizing agents.

According to a particular embodiment, the composition according to the invention comprises one or more chemical oxidizing agents.

According to another particular embodiment, the composition according to the invention does not comprise chemical oxidizing agents.

According to this embodiment, the composition according to the invention is preferably mixed at the moment of use with at least one composition comprising one or more chemical oxidizing agents.

For the purposes of the present invention, the term "chemical oxidizing agent" is understood to mean an oxidizing agent other than atmospheric oxygen.

The chemical oxidizing agent(s) (or bleaching agents) which may be used in the present invention may be chosen from hydrogen peroxide, urea peroxide, alkali metal bromates, persalts, such as perborates and persulfates, in particular sodium persulfate, potassium persulfate and ammonium persulfate, peracids and oxidase enzymes (with their optional cofactors), among which mention may be made of peroxidases, 2-electron oxidoreductases, such as uricases, and 4-electron oxygenases, such as laccases, and mixtures thereof; more preferentially, the chemical oxidizing agent(s) is/are chosen from hydrogen peroxide, persalts, and mixtures thereof, more preferably still hydrogen peroxide.

Preferably, when they are present in the composition according to the invention, the chemical oxidizing agent(s) is/are present in a total content ranging from 0.1% to 35% by weight, more preferentially from 0.5% to 25% by weight, even more preferentially from 1% to 15% by weight, relative to the weight of the composition.

According to a preferred embodiment, when they are present in the composition according to the invention, the chemical oxidizing agent(s) chosen from hydrogen peroxide, persalts and mixtures thereof is/are present in a total content ranging from 0.1% to 35% by weight, more preferentially from 0.5% to 25% by weight, even more preferentially from 1% to 15% by weight, relative to the weight of the composition.

Additives

The composition according to the invention may contain any adjuvant or additive usually used.

Among the additives which may be present in the composition according to the invention, mention may be made of reducing agents, thickeners, softeners, antifoams, moisturizers, UV-screening agents, peptizers, solubilizers, fragrances, anionic, cationic, nonionic or amphoteric polymers or mixtures thereof, antidandruff agents, antiseborrheic agents, vitamins and provitamins including panthenol, sunscreens, sequestrants, plasticizers, solubilizing agents, acidifying agents, mineral or organic thickeners, especially polymeric thickeners, antioxidants, hydroxy acids, fragrances and preserving agents.

Of course, those skilled in the art will take care to choose this or these optional additional compounds so that the advantageous properties intrinsically associated with the composition according to the invention are not, or not substantially, detrimentally affected by the envisioned addition(s).

The above additives may generally be present in an amount, for each of them, of between 0 and 20% by weight relative to the total weight of the composition.

Process

The present invention also relates to a process for dyeing keratin fibres, in particular human keratin fibres such as the hair, wherein the composition as described previously is applied to said fibres.

Preferably, the composition according to the invention is a composition for dyeing keratin fibres, such as the hair.

Preferably, the composition according to the invention comprises one or more oxidation bases, preferentially chosen from 2-methoxymethyl-para-phenylenediamine, 2-$-hydroxyethyl-para-phenylenediamine, 2-$\gamma$-hydroxypropyl-para-phenylenediamine, and their addition salts, their solvates and/or the solvates of their salts and mixtures thereof.

The composition according to the invention can be used on wet or dry keratin fibres, and also on all types of fair or dark, natural or dyed, permanent-waved, bleached or relaxed, fibres.

According to a particular embodiment of the process of the invention, the fibres are washed before application of the composition described above.

The application of the composition of the invention to the keratin fibres can be carried out by any conventional means, in particular by means of a comb, a fine brash, a coarse brush or with the fingers.

The dyeing process, i.e. application of the dye composition to the keratin fibres, is generally carried out at ambient temperature (between 15 and 25° C.).

The composition according to the invention may be applied to the keratin fibres for a leave-on time ranging from 30 to 60 minutes.

After application of the composition according to the invention, the keratin fibres may optionally undergo washing with a shampoo and/or be rinsed with water.

According to a particular embodiment, the dyeing process comprises at least the application, to said fibres, of a composition comprising:

at least one oxidation coupler chosen from 6-hydroxybenzomorpholine of formula (II) below, one of its addition salts, its solvates and/or solvates of its salts:

(II)

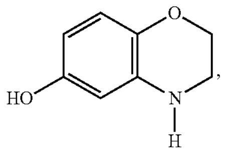

, at least one oxidation coupler chosen from hydroxyethyl-3,4-methylenedioxyaniline of formula (III) below, one of its addition salts, its solvates and/or solvates of its salts:

(III)

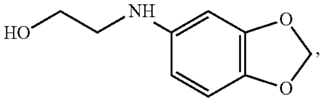

one or more compounds chosen from N,N-dicarboxymethylglutamic acid, its salts and mixtures thereof as described above, one or more oxidation bases as described above, preferably chosen from 2-methoxymethyl-para-phenylenediamine, 2-β-hydroxyethyl-para-phenylenediamine, 2-γ-hydroxypropyl-para-phenylenediamine, and their addition salts, their solvates and/or the solvates of their salts and mixtures thereof, one or more chemical oxidizing agents as described above.

According to another particular embodiment, the dyeing process comprises at least the application, to said fibres, of a composition obtained by mixing, at the moment of use:

at least one composition comprising:

at least one oxidation coupler chosen from 6-hydroxybenzomorpholine of formula (II) below, one of its addition salts, its solvates and/or solvates of its salts:

(II)

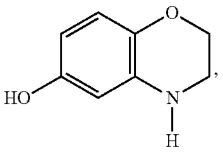

at least one oxidation coupler chosen from hydroxyethyl-3,4-methylenedioxyaniline of formula (III) below, one of its addition salts, its solvates and/or solvates of its salts:

(III)

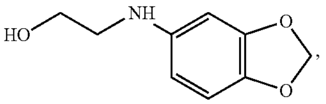

one or more compounds chosen from N,N-dicarboxymethylglutamic acid, its salts and mixtures thereof as described above, one or more oxidation bases as described above, preferably chosen from 2-methoxymethyl-para-phenylenediamine, 2-β-hydroxyethyl-para-phenylenediamine, 2-γ-hydroxypropyl-para-phenylenediamine, and their addition salts, their solvates and/or the solvates of their salts and mixtures thereof, and at least one composition comprising or more chemical oxidizing agents as described above, preferably hydrogen peroxide.

The oxidizing composition is preferably an aqueous composition. In particular, it comprises more than 5% by weight of water, preferably more than 10% by weight of water and even more advantageously more than 20% by weight of water.

It may also comprise one or more organic solvents chosen from those listed previously; these solvents more particularly representing, when they are present, from 1% to 40% by weight and preferably from 5% to 30% by weight, relative to the weight of the oxidizing composition.

The oxidizing composition also preferably comprises one or more acidifying agents. Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

The oxidizing composition may additionally comprise fatty substances such as those described hereinabove, preferably chosen from fatty alcohols, liquid hydrocarbons comprising more than 16 carbon atoms and mixtures thereof, surfactants and polymers.

Usually, the pH of the oxidizing composition, when it is aqueous, is less than 7.

Preferably, the oxidizing composition comprises hydrogen peroxide as oxidizing agent, in aqueous solution, the concentration of which ranges, more particularly, from 0.1% to 50%, more particularly between 0.5% and 20% and even more preferentially between 1% and 15% by weight, relative to the weight of the oxidizing composition.

Preferably, at least one of the (dyeing or oxidizing) compositions is aqueous.

When the oxidizing composition is extemporaneously mixed with the dyeing composition according to the invention, the pH of the mixture obtained is preferably between 8 and 11, more preferentially between 9 and 10.7.

The pH may be adjusted to the desired value by means of acidifying or alkalinizing agents, or alternatively using buffer systems, as defined above.

The present invention also relates to the use of the composition according to the invention as described previously for dyeing keratin fibres, in particular human keratin fibres such as the hair.

The invention furthermore relates to a multicompartment device comprising at least a first compartment containing the composition according to the invention as described hereinabove, and at least a second compartment containing one or more oxidizing agents as described hereinafter, preferably hydrogen peroxide.

The following examples serve to illustrate the invention without, however, exhibiting a limiting nature.

EXAMPLES

In the examples which follow, all the amounts are shown, unless otherwise indicated, as percentage by weight of active material, with respect to the total weight of the composition.

Compositions A0, A1 and A2 (dye compositions) and composition B (oxidizing composition B) were prepared from the ingredients whose contents are indicated in the tables below (% active material unless otherwise mentioned):

TABLE 1

| | Composition A0 (invention) | Composition A1 (comparative) | Composition A2 (comparative) |
|---|---|---|---|
| Ascorbic acid | 0.25 | 0.25 | 0.25 |
| 2,4-Diaminophenoxyethanol HCl | 0.1 | 0.1 | 0.1 |
| Meadowsweet oil | 0.1 | 0.1 | 0.1 |
| m-Aminophenol | 0.3 | 0.3 | 0.3 |
| Camellia oil | 0.1 | 0.1 | 0.1 |
| Sunflower oil | 0.1 | 0.1 | 0.1 |
| Polysorbate-21 | 2.4 | 2.4 | 2.4 |
| 2-Amino-3-hydroxypyridine | 0.04 | 0.04 | 0.04 |
| Caprylyl/capryl glucoside | 2.4 | 2.4 | 2.4 |
| Polyquaternium-67 | 0.2 | 0.2 | 0.2 |
| Passionflower oil | 0.1 | 0.1 | 0.1 |
| 6-Hydroxyindole | 0.05 | 0.05 | 0.05 |
| Hydroxybenzomorpholine | 2.1 mmol | 4.2 mmol | — |
| Steareth-20 | 3.9 | 3.9 | 3.9 |
| Sodium metabisulfite | 0.45 | 0.45 | 0.45 |
| Toluene-2,5-diamine (and) thioglycerine | 0.9 | 0.9 | 0.9 |
| Bis(2-hydroxyethyl)-p-phenylenediamine sulfate | 0.06 | 0.06 | 0.06 |
| Hydroxyethyl-3,4-methylenedioxyaniline HCl | 2.1 mmol | — | 4.2 mmol |
| Liquid paraffin | 59.7 | 59.7 | 59.7 |
| Steareth-2 | 1.1 | 1.1 | 1.1 |
| Tetrasodium glutamate diacetate (GLDA) | 0.1 | 0.1 | 0.1 |
| Ethanolamine | 4.8 | 4.8 | 4.8 |
| Fragrance | q.s. | q.s. | q.s. |
| Water | q.s. 100 | q.s. 100 | q.s. 100 |

TABLE 2

| | Composition B |
|---|---|
| Sodium salicylate | 0.035 |
| Tocopherol | 0.1 |
| Tetrasodium pyrophosphate | 0.04 |
| Hydrogen peroxide | 6 |
| Cetearyl alcohol | 6 |
| Hexadimethrine chloride | 0.15 |
| Polyquaternium-6 | 0.2 |
| Liquid paraffin | 20 |
| Tetrasodium etidronate | 0.06 |
| Phosphoric acid | q.s. pH 2.2 |
| PEG-4 rapeseedamide | 1.2 |
| Glycerol | 0.5 |
| Steareth-20 | 5 |
| Water | q.s. 100 |

Protocol:

At the moment of use, the dye compositions A0, A1 and A2 are mixed with 1 times their weight of the oxidizing composition B (6 g % $H_2O_2$).

Each of the mixtures is then applied to locks of hair containing 90% natural white (NW) hair and moderately sensitized (AS20) hair, in a proportion of 5 g of mixture per 1 g of hair.

After a leave-on time of 30 minutes on a hot plate at 27° C., the hair is rinsed, washed with L'Oreal Professional Pro Classics universal concentrated shampoo, diluted to 10%, and dried.

Colorimetric measurements were performed using a KONICA MINOLTA CM-3600A spectropolarimeter (illuminant D65, angle 10°, specular component included) in the CIELab system.

In this system, L* represents the lightness: the lower the value of L*, the deeper, more powerful and more intense the colouring obtained. The chromaticity is measured by the values a* and b*, a* representing the green/red colour axis and b* the blue/yellow colour axis.

The selectivity is represented by the colour difference ΔE between the locks of natural white (NW) hair and the locks of moderately sensitized (AS20) hair.

The ΔE value is calculated according to the following equation:

$$\Delta E=\sqrt{(L^*-L_0^*)^2+(a^*-a_0^*)^2+b^*-b_0^*)^2}$$

In this equation, L*, a* and b* represent the values measured on dyed natural hair (NW) and L0*, a0* and b0* represent the values measured on dyed sensitized hair (AS20).

The greater the value of ΔE, the greater the colour difference between the locks of natural hair and the locks of sensitized hair, which represents less homogeneity of the colouring, and therefore greater selectivity.

The lower the value of ΔE, the lower, and hence better, the selectivity (homogeneous colouring).

Selectivity:

The selectivity is represented by the colour difference ΔE between the natural and sensitized locks: the lower the value of ΔE, the better the selectivity.

The results are given in Table 3 below.

TABLE 3

| | Hair type | L* | a* | b* | ΔE |
|---|---|---|---|---|---|
| Invention | NW | 20.06 | 0.76 | −0.05 | |
| (mixture A0 + B) | AS20 | 17.97 | 0.11 | −0.6 | 2.26 |
| Comparative 2 | NW | 21.03 | 0.8 | 0.51 | |
| (mixture A2 + B) | AS20 | 16.65 | 0.29 | −0.26 | 4.48 |
| Comparative 1 | NW | 21.79 | 1.29 | 0.88 | |
| (mixture A1 + B) | AS20 | 17.71 | 0.39 | −0.19 | 4.31 |

The composition according to the invention leads to a lower value of ΔE, thus to a better selectivity, compared to the comparative compositions 1 and 2 according to the prior art.

The colourings obtained with the composition according to the invention are therefore more homogeneous than the colourings obtained with the comparative compositions.

The invention claimed is:

1. A cosmetic composition comprising:

at least one oxidation coupler chosen from 6-hydroxybenzomorpholine of formula (II) below, one of its addition salts, its solvates and/or solvates of its salts in a content ranging from 0.001% to 3% by weight, relative to the weight of the composition:

(II)

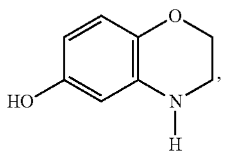

and at least one oxidation coupler chosen from hydroxyethyl-3,4-methylenedioxyaniline of formula (III) below, one of its addition salts, its solvates and/or solvates of its salts in a content ranging from 0.001% to 3% by weight, relative to the weight of the composition:

(III)

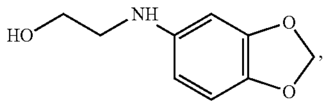

and one or more compounds chosen from alkali metal salts of N,N-dicarboxymethylglutamic acid in a content ranging from 0.05% to 5% by weight, relative to the total weight of the composition.

2. The composition according to claim 1, characterized in that the total content of oxidation couplers chosen from 6-hydroxybenzomorpholine of formula (II), one of its addition salts, its solvates and/or solvates of its salts, and hydroxyethyl-3,4-methylenedioxyaniline of formula (III), one of its addition salts, its solvates and/or solvates of its salts, ranges from 0.1% to 3% by weight, relative to the weight of the composition.

3. The composition according to claim 1, characterized in that the weight ratio between the content of 6-hydroxybenzomorpholine of formula (II), one of its addition salts, its solvates and/or solvates of its salts, and the content of hydroxyethyl-3,4-methylenedioxyaniline of formula (III), one of its addition salts, its solvates and/or the solvates of its salts is between 0.1 and 10.

4. The composition according to claim 1, characterized in that it additionally comprises one or more couplers different from 6-hydroxybenzomorpholine of formula (II), one of its addition salts, its solvates and/or solvates of its salts, and hydroxyethyl-3,4-methylenedioxyaniline of formula (III), one of its addition salts, its solvates and/or the solvates of its salts.

5. The composition according to claim 1, characterized in that it comprises one or more oxidation bases.

6. The composition according to claim 5, characterized in that the oxidation base(s) is/are present in a content ranging from 0.001% to 20% by weight relative to the weight of the composition.

7. The composition according to claim 1, further comprising at least one fatty substance.

8. The composition according to claim 1, further comprising at least one liquid fatty substance.

9. The composition according claim 1, further comprising at least one solid fatty substance.

10. The composition according to claim 1, further comprising at least one surfactant.

11. The composition according to claim 1, further comprising one or more sequestrants.

12. The composition according to claim 1, further comprising at least one alkaline agent.

13. The composition according to claim 1, characterized in that it additionally comprises one or more chemical oxidizing agents.

14. A process for dyeing keratin fibres, comprising at least the application, to said fibres, of a composition as defined according to claim 13.

15. The process according to claim 14, wherein the composition is obtained by mixing, at the moment of use:

at least one composition as defined by:

at least one oxidation coupler chosen from 6-hydroxybenzomorpholine of formula (II) below, one of its addition salts, its solvates and/or solvates of its salts in a content ranging from 0.001% to 3% by weight, relative to the weight of the composition:

(II)

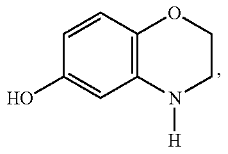

and at least one oxidation coupler chosen from hydroxyethyl-3,4-methylenedioxyaniline of formula (III) below, one of its addition salts, its solvates and/or solvates of its salts in a content ranging from 0.001% to 3% by weight, relative to the weight of the composition:

(III)

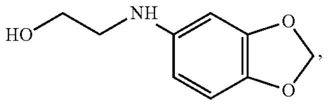

and one or more compounds chosen from alkali metal salts of N,N-dicarboxymethylglutamic acid in a content ranging from 0.05% to 5% by weight, relative to the total weight of the composition, and at least one composition comprising one or more chemical oxidizing agents.

16. A multicompartment device comprising at least a first compartment containing the composition as defined according to claim 1, and at least a second compartment containing one or more oxidizing agents.

17. The composition according to claim 1, characterized in that it additionally comprises one or more couplers different from 6-hydroxybenzomorpholine of formula (II), one of its addition salts, its solvates and/or solvates of its salts and hydroxyethyl-3,4-methylenedioxyaniline of formula (III), one of its addition salts, its solvates and/or solvates of its salts, said couplers being chosen from meta-phenylenediamines, meta-aminophenols, meta-diphenols, naphthalene-based coupling agents, heterocyclic coupling agents, and their corresponding addition salts, their solvates and/or the solvates of their salts.

18. The composition according to claim 1, characterized in that it further comprises one or more oxidation bases chosen from para-phenylenediamines, bis(phenyl)alkylenediamines, para-aminophenols, ortho-aminophenols, heterocyclic bases, and the corresponding addition salts, their solvates, the solvates of their salts and mixtures thereof.

* * * * *